United States Patent
Hino

(10) Patent No.: US 8,033,992 B2
(45) Date of Patent: Oct. 11, 2011

(54) ELECTRONIC ENDOSCOPE APPARATUS

(75) Inventor: Kazuhiko Hino, Saitama (JP)

(73) Assignee: Fujinon Corporation, Saitama (JP)

( * ) Notice: Subject to any disclaimer, the term of this patent is extended or adjusted under 35 U.S.C. 154(b) by 810 days.

(21) Appl. No.: 12/032,399

(22) Filed: Feb. 15, 2008

(65) Prior Publication Data

US 2008/0242936 A1     Oct. 2, 2008

(30) Foreign Application Priority Data

Mar. 27, 2007   (JP) ............................... P2007-080493

(51) Int. Cl.
*A61B 1/04*   (2006.01)
*A61B 1/00*   (2006.01)

(52) U.S. Cl. ........................................ 600/132; 600/144

(58) Field of Classification Search .................. 600/132, 600/139, 140, 144; 604/526, 527; 385/76, 385/101, 104, 106, 112

See application file for complete search history.

(56) References Cited

U.S. PATENT DOCUMENTS

| | | | |
|---|---|---|---|
| 4,690,175 A | | 9/1987 | Ouchi et al. |
| 4,759,346 A | * | 7/1988 | Nakajima ..................... 600/110 |
| 4,977,887 A | * | 12/1990 | Gouda .......................... 600/144 |
| 7,695,429 B2 | * | 4/2010 | Hino ............................. 600/132 |
| 2002/0032369 A1 | | 3/2002 | Takase |
| 2005/0267333 A1 | | 12/2005 | Hino |

FOREIGN PATENT DOCUMENTS

| | | |
|---|---|---|
| CN | 2544446 Y | 4/2003 |
| EP | 1600101 A | 11/2005 |
| JP | 8-76025 A | 3/1996 |
| JP | 8-76026 A | 3/1996 |
| JP | 2000-229059 A | 8/2000 |

OTHER PUBLICATIONS

Mimori, Naotake, Flexible Portion Structure of Endoscope, Aug. 22, 2000, Published by PAJ (JPO): Publication No. 2000-229059, pp. 1-6 (Detailed Description) and pp. 1-3 (Drawings).*
Chinese Office Action dated Aug. 28, 2009, issued in the corresponding Chinese Application No. 200810005610.5.

* cited by examiner

*Primary Examiner* — Linda Dvorak
*Assistant Examiner* — Alireza Nia
(74) *Attorney, Agent, or Firm* — Birch, Stewart, Kolasch & Birch, LLP

(57) ABSTRACT

An electronic endoscope apparatus comprises: an intermediate member attached to a first cable of an electronic endoscope; a connector connected to a light source portion or to a processor portion; a second cable extending from the intermediate member and connecting to the connector; and a flexible outer-sheath for the second cable, the flexible outer-sheath comprising a flexible spiral tube and a resin outer skin provided on an exterior of the flexible spiral tube, wherein the flexible spiral tube is formed by spirally winding a strip body having engaging-projections respectively provided on its both side portions, so as to make the engaging-projections be engaged with each other and form a movable space which allows one of the engaging-projections to move with respect to the other one of the engaging-projections, and wherein an entirety of the flexible spiral tube is bendable with expansion and contraction of a space between the engaging-projections within the movable space.

2 Claims, 5 Drawing Sheets

ELECTRONIC ENDOSCOPE APPARATUS

BACKGROUND OF THE INVENTION

1. Field of the Invention

The present invention relates to an electronic endoscope and, more particularly, to the structure of each of cables for connecting between a light-source-side connector and a processor portion, between an intermediate member of an electronic endoscope and the light-source-side connector, and between the intermediate member and a processor portion.

2. Description of the Related Art

A related electronic endoscope apparatus irradiates light, which is supplied from a light source portion (light source unit) through a lightguide, from a front end portion of an electronic endoscope (scope). Then, an observation object illuminated with the irradiated light is imaged by, for example, a CCD (Charge Coupled Device) serving as a solid-state image pickup device mounted at the front end thereof. Subsequently, an image pickup signal output from the CCD is supplied to a processor unit through a cable. Then, predetermined signal processing is performed on the image pickup signal at the processor unit. Thus, an image of the observation object, such as a digestive organ, can be displayed on a monitor.

FIG. 5 illustrates the configuration of a part of a related electronic endoscope apparatus. As illustrated in FIG. 5, the related electronic endoscope apparatus has a light source unit 1 and a processor unit 2. A cable 3 of an electronic endoscope (not shown) is connected to the light source unit 1 through a light source connector 4. A branch cable 5 branched off from the light source connector 4 is connected to the processor unit 2. That is, a lightguide and a signal line are provided in the cable 3 to extend from a front end portion of the electronic endoscope. The lightguide is connected to the light source unit 1 through the light source connector 4, while the signal line is provided in the branch cable 5 through the light source connector 4 and is connected to the processor unit 2 by inserting the electric connector 6 into a connector receptacle 7a.

Further, such a kind of an electronic endoscope apparatus is configured so that different kinds of electronic endoscopes can be connected to the processor unit 2. Thus, the processor unit 2 is provided not only with a connector receptacle 7a, to which the aforementioned electric connector 6 is connected, but with another connector receptacle 7b to which a connector of another kind of an electronic endoscope is connected.

FIG. 6 illustrates the configuration of an outer-sheath of the branch cable 5 is displayed. This outer-sheath is constituted by a spiral tube 8 formed by spirally winding an elongated metallic strip body, a net 9 which covers the exterior of the spiral tube 8, and a synthetic resin outer skin 10 which covers the exterior of the net 9.

However, the branch cable 5 used in the related electronic endoscope apparatus has a structure in which the spiral tube 8 is covered with the net 9, as illustrated in FIG. 6. Consequently, the branch cable 5 is relatively hard, so that the cable 5 can be neither freely bent nor largely twisted. Thus, sometimes, the electric connector 6 cannot smoothly be attached to the connector receptacle 7a. That is, because an attaching position (position in a rotational direction), at which the electric connector 6 is attached to the connector receptacle 7a, is preliminarily determined, the electric connector 6 sometimes cannot smoothly be inserted into the predetermined position in a case where the branch cable 5 is hard.

Further, in a case where different kinds of electronic endoscopes are connected to the processor unit 2, the attaching position of the light source connector 4 does not change, whereas the attaching position of the electric connector 6 is changed from the position of the connector receptacle 7a to that of the connector receptacle 7b. Even in such a case, the related electronic endoscope apparatus has a problem that because the branch cable 5 is relatively hard, the electric connector 6 cannot smoothly be inserted into the connector receptacle.

On the other hand, as described in JP-A-8-76025, some related device is configured so that a junction portion of a cable of an endoscope has a rotating mechanism. FIG. 7 illustrates the configuration of this endoscope. This endoscope is configured so that a cable 13 provided to extend from an operating portion 12 has a junction portion 14, that branch cables 15 and 16 are branched off from the junction portion 14, and that the light source connector 17 is attached to one of the branch cables 15, while the electric connector 18 is attached to the other branch cable 16. Additionally, a rotating mechanism constituted by a sliding groove and a pin is provided in the junction portion 14. Consequently, the branch cables 15 and 16 are rotated by the rotating mechanism with respect to the cable 13. Thus, the twist of the cable can be absorbed by the rotating mechanism.

However, even in such a configuration, in a case where the branch cables 15 and 16 are fixed to the junction portion 14, and where the light source connector 17 is fixed to the light source unit, the movement (drawing-out) of the electric connector 18 is restricted. On the other hand, in a case where the branch cables 15 and 16 are fixed to the junction portion 14, and where the electric connector 18 is fixed to the processor unit, the movement (drawing-out) of the light source connector 18 is restricted. Thus, the related electric endoscope apparatus has a problem that the light source connector 17 and the complicated rotating mechanism cause high cost.

SUMMARY OF THE INVENTION

The invention is accomplished in view of the aforementioned problems. An object of the invention is to provide an electronic endoscope apparatus enabled to obtain sufficient bend and twist of a cable, which is to be connected to a connector, with a simple configuration, without employing a complicated configuration.

To achieve the foregoing object, according to a first aspect of the invention, there is provided an electronic endoscope apparatus comprising: an intermediate member attached to a first cable of an electronic endoscope; a first connector connected to a light source portion or to a processor portion; a second cable extending from the intermediate member and connecting to the connector; and a flexible outer-sheath for the second cable, the flexible outer-sheath comprising a flexible spiral tube and a resin outer skin provided on an exterior of the flexible spiral tube, wherein the flexible spiral tube is formed by spirally winding a strip body having engaging-projections respectively provided on its both side portions, so as to make the engaging-projections be engaged with each other and form a movable space which allows one of the engaging-projections to relatively move with respect to the other one of the engaging-projections, and wherein an entirety of the flexible spiral tube is bendable with expansion and contraction of a space between the engaging-projections within the movable space.

According to a second aspect of the invention, there is provided the electronic endoscope apparatus, wherein the intermediate member is a light source connector to be connected to the light source portion; and the first connector is an electronic connector to be connected to the processor portion.

According to a third aspect of the invention, there is provided the electronic endoscope apparatus, further comprising a sleeve that has a spiral protrusion formed on its periphery and is screwed and connected into an inside of the flexible spiral tube, wherein the sleeve is fixed to the light source portion or to the processor portion.

With the aforementioned configurations, the entire flexible spiral tube is bent and twisted by an expansion-and-contraction operation in which the engaging projections engaged with each other of the flexible spiral tube serving as the outer-sheath move in the movable space. Thus, cable can easily be bent and twisted, as compared with the related cable.

DETAILED DESCRIPTION OF THE INVENTION

Figure 1:
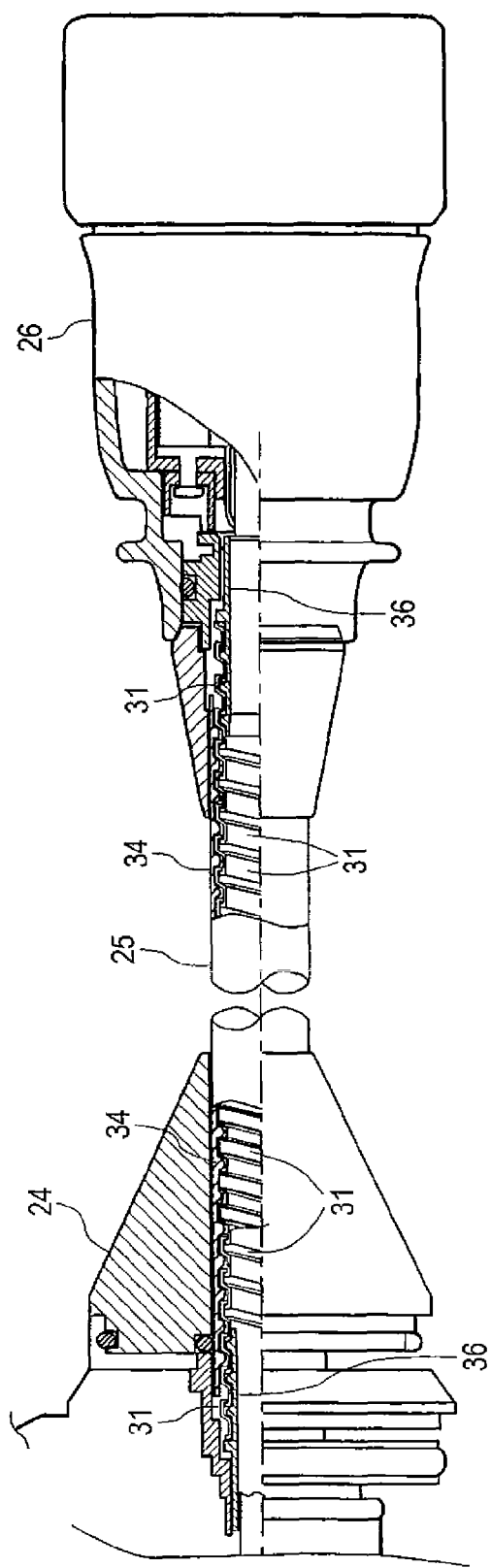
FIG. 1 is a partial cross-sectional view illustrating the configuration of a branch cable provided between a light source connector and an electric connector of an electronic endoscope apparatus according to an embodiment of the invention.
Figure 2:
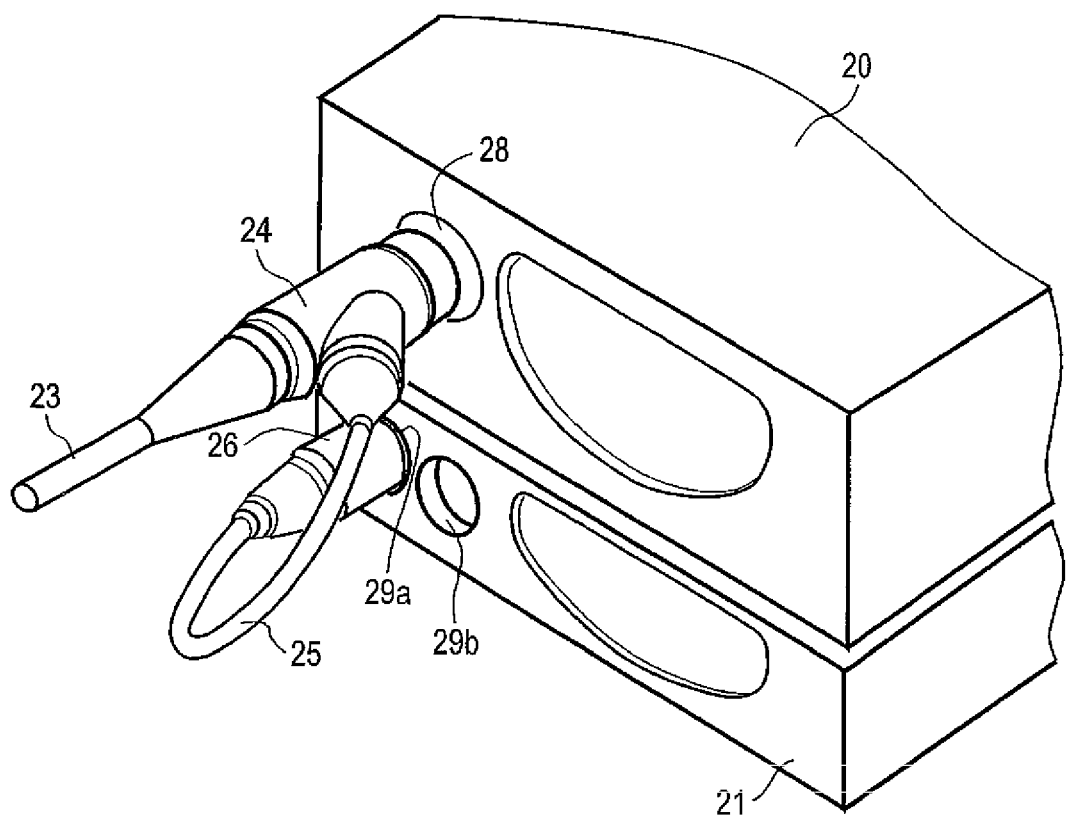
FIG. 2 is a perspective view illustrating a connection state in which a cable is connected to a connector of each of a light source unit and a processor unit according to the embodiment of the invention.
Figure 7:
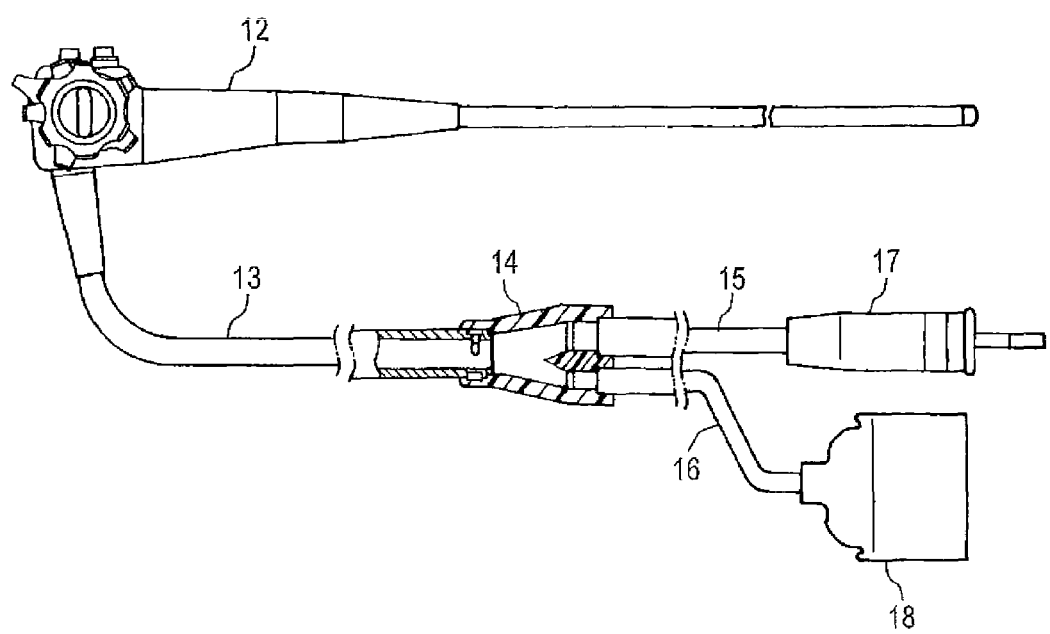
FIG. 7 is a partial cross-sectional view illustrating the configuration of a cable and a connector connected to an endoscope of the related electronic endoscope apparatus.

FIGS. 1 to 4 illustrate the configuration of an electronic endoscope apparatus according to an embodiment of the invention. In this electronic endoscope apparatus, a light source unit 20 and a processor unit 21 are disposed as illustrated in FIG. 2. An electronic endoscope (scope) (not shown) is connected to these units. That is, as illustrated in FIG. 7, a light source connector 24 is provided at an end portion of a cable 23 that is provided to extend from an operating portion of the electronic endoscope. A branch cable 25 is provided to be branched off from the light source connector 24. An electric connector 26 is provided at an end portion of the branch cable 25. In this case, the light source connector 24 serves as an intermediate member. On the other hand, a connector receptacle 28, to which the light source connector 24 is connected, is provided in the light source unit 20. A connector receptacle 29a to which the electric connector 26 is connected, and another connector receptacle 29b to which another electric connector is connected, are provided in the processor unit 21.

Figure 3:
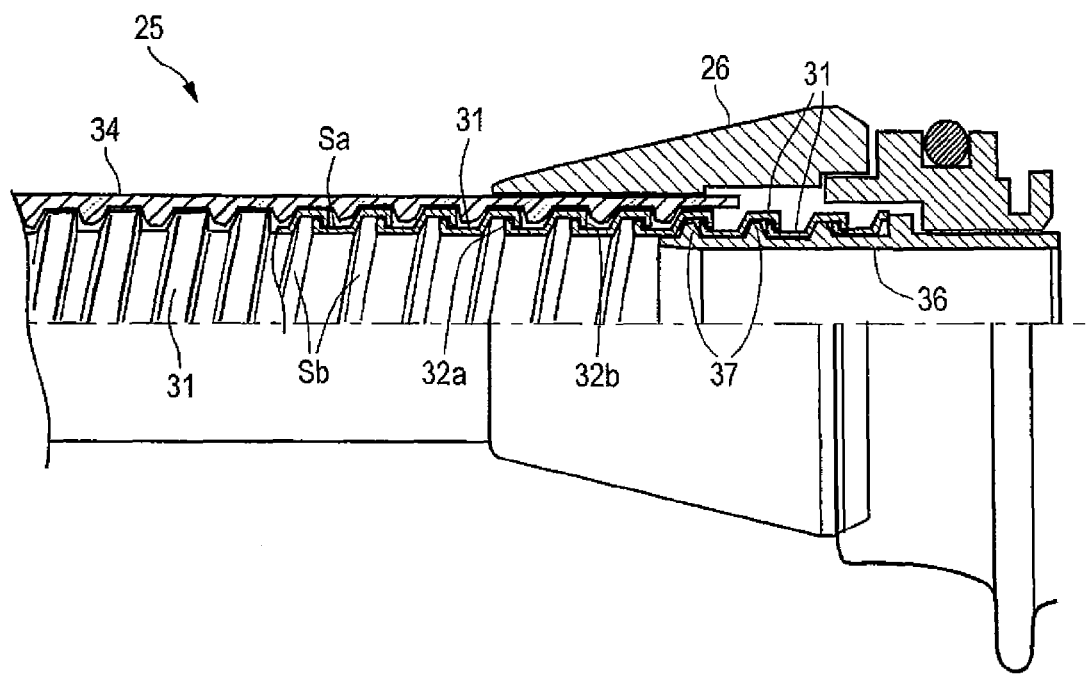
FIG. 3 is a partially cross-sectional view illustrating the configuration of a connection portion between the branch cable and the electric connector according to the embodiment of the invention.
Figure 4:
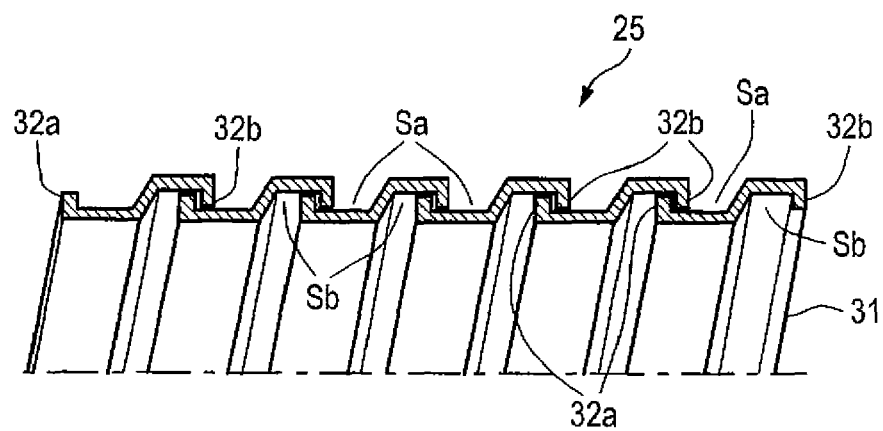
FIG. 4 is an enlarged cross-sectional view illustrating the configuration of a flexible spiral tube applied to an outer-sheath of the branch cable according to the embodiment of the invention.
Figure 5:
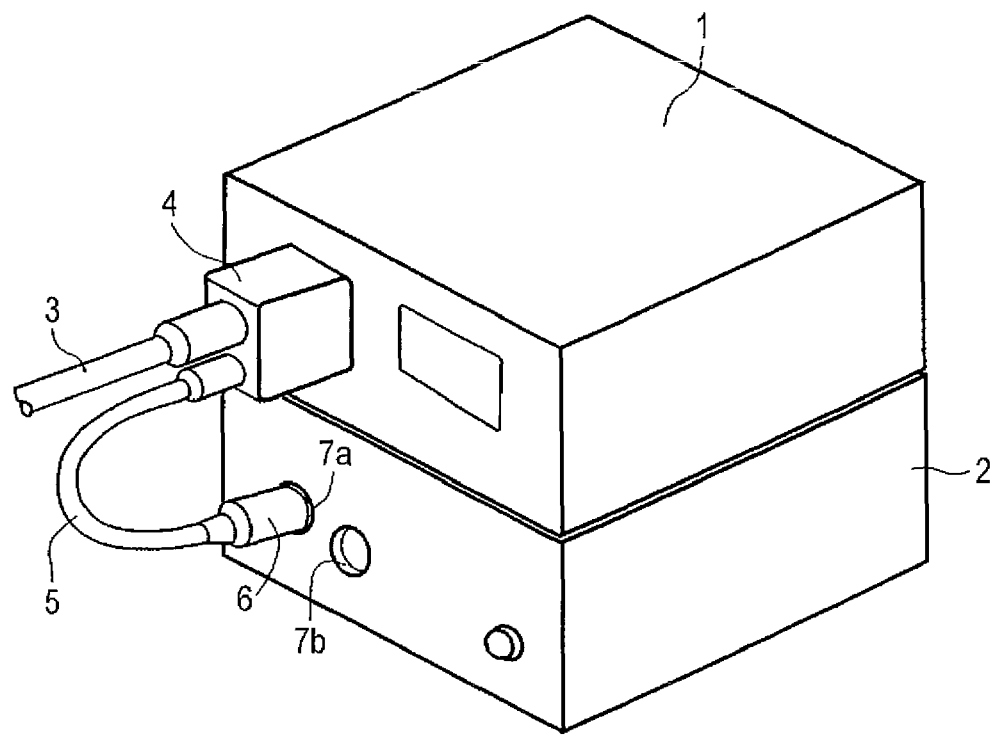
FIG. 5 is a perspective view illustrating a connection state in which a cable is connected to a connector of a light source unit and a processor unit that constitute a related electronic endoscope apparatus.
Figure 6:
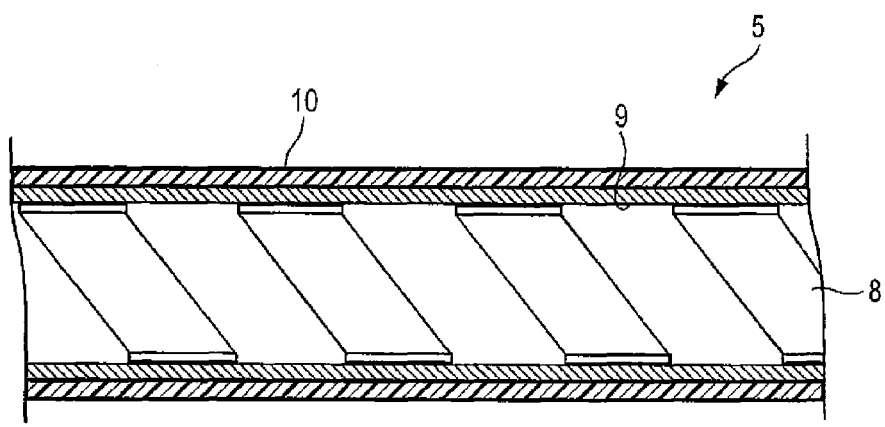
FIG. 6 is across-sectional view illustrating the configuration of a related branch cable.

FIG. 1 illustrates the configuration of the branch cable 25, which is provided to extend from the light source connector 24, and the electric connector 26. FIG. 3 illustrates the configuration of a connection portion between the branch cable 25 and the electric connector 26. FIG. 4 illustrates the configuration of a flexible spiral tube. According to the present embodiment, a flexible outer-sheath is used as an outer-sheath of the branch cable 25. The flexible outer-sheath has a flexible spiral tube 31 shown in FIG. 4. The flexible spiral tube 31 is obtained by winding an elongated strip body like a spiral. This strip body is transversely cross-sectionally shaped by being bent to form a concave portion, which has a movable space Sa at an upper part thereof, and a convex portion which has a movable space Sb at a lower part thereof. Engaging projections 32a, 32b are provided at both side portions (both side ends) of the strip body, respectively. The flexible spiral tube 31 is formed by spirally winding the strip body while the engaging projection 32a provided at one of the side portions of the strip body is engaged with the engaging projection 32b provided at the other side portion thereof. According to the flexible spiral tube 31, the engaging projection 32b moves in the movable space Sa, while the engaging projection 32b moves in the movable space Sb. Thus, the spiral tube itself expands and contracts. Consequently, the entire spiral tube is bent and can be twisted.

In the present embodiment, a sleeve 36 is used in attaching the flexible spiral tube 31 to the light source connector 24 and the electric connector 26, as illustrated in FIG. 3. A spiral projection (screw) 37 is formed on the periphery of the sleeve 36. The spiral projection 31 is screwed and connected into the movable space Sb provided in the flexible spiral tube 31 while an adhesive agent is poured into a space between the sleeve 36 and the flexible spiral tube 31. Thus, the sleeve 36 is attached to the flexible spiral tube 31. Also, the sleeve 36 is fixed to a support portion of each of the electric connector 26 and the light source connector 24. Consequently, the flexible spiral tube 31 is held at both ends thereof. That is, although it has been considered to fix the flexible spiral tube 31 to the connectors by being soldered thereto so as to maintain the electric continuity between the cable and each of the connectors, the attachment of the cable to each of the connector can be achieved using the sleeve 36, without time-consuming soldering, while maintaining the electric continuity therebetween.

As illustrated in FIG. 3, the flexible spiral tube 31 is covered with an outer skin 34 formed of a synthetic resin tube. The outer skin 34 can be made of an olefin elastomer, a material obtained by forming a thermosetting resin (top coat) on a urethane resin, a silicon rubber (silicon resin), or a fluorine resin. The outer skin 34, which is provided on the flexible spiral tube 31, is fixed to the electric connector 26 and the light source connector 24 by a fixing member.

With such a configuration of the present embodiment, the engaging projections 32a, 32b engaged with each other move, expand and contract in the branch cable 25 having the flexible spiral tube 31 and the outer skin 34 as an outer-sheath. Thus, the branch cable 25 is favorably bent and twisted. Even in either case where the branch cable 25 is connected to the connector receptacle 29a or 29b, the drawing-around of the branch cable 25 is facilitated. Thus, an operation of connecting the cable to the electric connector 26 can smoothly be achieved.

In the foregoing description of the embodiment, the electric connector 26 branched from the light source connector 24 serving as the intermediate member has been described. As illustrated in FIG. 7, some related electronic endoscope apparatus is configured so that a cable is branched off from a junction portion serving as the intermediate member. In this case, the aforementioned outer-sheath including the flexible spiral tube 31 and the outer skin 34 can be disposed on a cable between the junction portion and the light source connector or to a cable between the junction portion and the electric connector.

In the foregoing description of the aforementioned embodiment, it has been described that the light source unit 20 is provided separately from the processor unit 21. However, the invention can be applied to an electronic endoscope apparatus configured so that a light source unit and a processor unit are formed integrally with each other into an apparatus (processor apparatus).

According to the first or second electronic endoscope apparatus of the invention, the flexible spiral tube is used as the outer-sheath. Additionally, a net used in the related electronic endoscope apparatus is eliminated. Thus, the invention has advantages that the cable to be connected to the connector can obtain sufficient bend and twist with a simple configuration, and without employing a complicated configuration, and that high cost is not caused. Further, according to the third electronic endoscope apparatus of the invention, the connection and the fixing of the flexible spiral tube to the connector can be simply and surely achieved.

The entire disclosure of each and every foreign patent application from which the benefit of foreign priority has been claimed in the present application is incorporated herein by reference, as if fully set forth.

What is claimed is:

1. An electronic endoscope apparatus comprising:
an intermediate member attached to a first cable of an electronic endoscope;
a first connector connected to a light source portion or to a processor portion;
a second cable extending from the intermediate member and connecting to the connector;
a flexible outer-sheath for the second cable, the flexible outer-sheath comprising a flexible spiral tube and a resin outer skin provided on an exterior of the flexible spiral tube; and
a sleeve having a spiral protrusion formed on its periphery and screwed and connected into an inside of the flexible spiral tube,
wherein the sleeve is fixed to the light source portion or to the processor portion,
wherein the flexible spiral tube is formed by spirally winding a strip body having engaging-projections respectively provided on its both side portions, so as to make the engaging-projections be engaged with each other and form a movable space which allows one of the engaging-projections to relatively move with respect to another one of the engaging-projections, and
wherein an entirety of the flexible spiral tube is bendable with expansion and contraction of a space between the engaging-projections within the movable space.

2. The electronic endoscope apparatus according to claim 1,
wherein the intermediate member is a light source connector to be connected to the light source portion; and
the first connector is an electronic connector to be connected to the processor portion.

* * * * *